United States Patent [19]

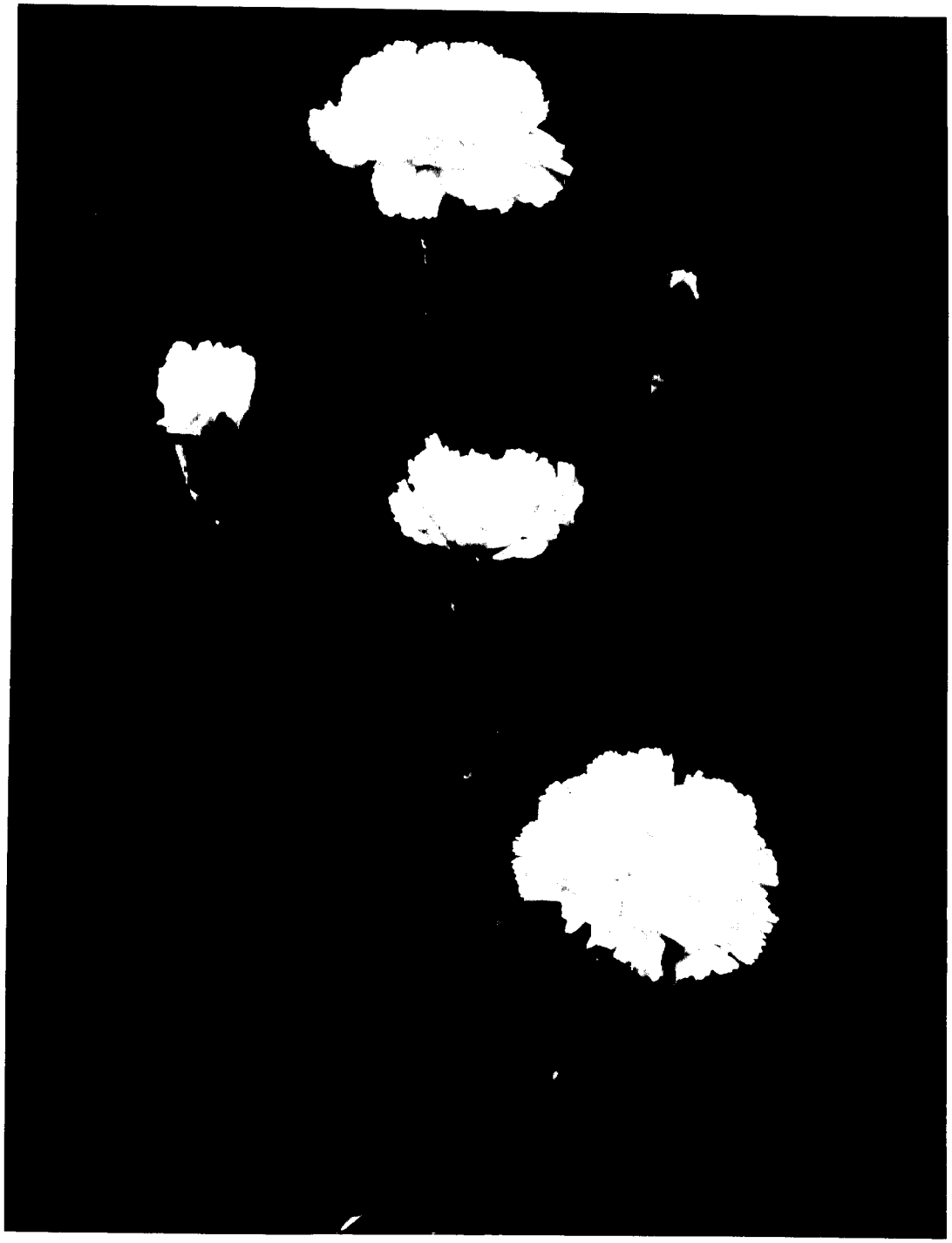

Barberet et al.

[11] Patent Number: Plant 5,784

[45] Date of Patent: Aug. 19, 1986

[54] CARNATION NAMED LONDORGA

[75] Inventors: Nicole Barberet; Yves Ducloux, both of Antibes, France

[73] Assignee: Laboratoire de Physiologie Vegetale de la Londe, La Londe, France

[21] Appl. No.: 613,712

[22] Filed: May 24, 1984

[51] Int. Cl.[4] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler; John B. Lungmus

[57] ABSTRACT

A new variety of standard carnation distinguished by its profuse production of medium sized, dome shaped flowers of a very light overall color, the petals of which are striated with very thin red and white lines, the plant having a tall, vigorous, upright and rigid growth habit, an abundant production of foliage and a strong resistance to *Fusarium oxysporum.*

1 Drawing Figure

BACKGROUND OF THE NEW PLANT

Our new standard carnation variety originated as a seedling at our breeding facilities at La Londe-Les-Maures-Var., France, and resulted from our crossing of two unnamed and unpatented varieties maintained in our breeding plant collection at La Londe. The object of this crossing was to produce an improved carnation plant having good quality and nice flower form and coloration suitable for commercial cut flower production. This particular seedling was selected by us for propagation and test because of the unusual color characteristics of its very light yellow blooms, and reproduction was done under our direction at La Londe by means of cuttings from the parent plant. Further propagation of this new variety at La Londe through several successive generations, by means of in vitro propagation and cuttings, has demonstrated that the novel characteristics of the parent seedling hold true from generation to generation and appear to be firmly fixed.

DESCRIPTION OF THE DRAWING

Our new carnation variety is illustrated by the accompanying full color photographic drawing which shows the inflorescence of a fully grown plant, the view including buds in various stages of opening, as well as fully opened flowers, the color rendition being as nearly true as is reasonably possible to obtain by means of conventional photographic procedures from subjects of such a light yellow coloration.

DESCRIPTION OF THE NEW PLANT

The following is a detailed description of our new carnation cultivar based upon observation of plants growing under conventional procedures at La Londe-Les-Maures-Var., France, the color designations being according to The R.H.S. Colour Chart published by The Royal Horticultural Society of London, England.

THE PLANT

Origin: Seedling.

Parentage:

*Seed parent.*—An unnamed and unpatented variety No. 345 J;

*Pollen parent.*—An unnamed and unpatented No. 6 J 8; these plants having been selected from breeding material maintained and recorded at our laboratory at La Londe.

Classification:

*Botanic.—Dianthus caryophyllus.*

*Commercial.*—Standard carnation.

Form: An erect bush with at least four stems emitted near the ground.

Height: About 125 cm. in average at ten months.

Growth: Vigorous and upright with strong, rigid stems.

Branching: Rather well branched.

Pinching requirement: Pinching of the main axis between the fourth and sixth nodes from the base.

Foliage:

*Quantity.*—Abundant with more than 120 leaves.

*Leaf size.*—Normal, about 14 cm. long and 1.4 cm. wide in average.

*Leaf shape.*—Amplexicaul and oblong with acuminate apex.

*Texture.*—Leathery.

*Ribs, veins and rachis.*—Hardly noticeable.

*Color.*—Upper Side — 189B. Under Side — 189B.

THE BUD

Size: Medium, averaging about 2 cm. in diameter and about 3.7 cm. in length.

Form:

*Ovoid.*—Nearly cylindrical.

Opening rate: Normal.

Color of petals:

*When sepals first divide and when they begin to unfurl.*—The same as in full bloom.

Sepals:

*Number.*—Mostly five and hooded over the bud.

*Shape.*—Rather broad, joined at the lower part and becoming acute at the upper end.

*Character.*'The sepals curl back when the flowers open.

*Color.*—Inside — Greenish white. Outside — 137D and 145B.

*Striae.*—Longitudinally striated.

Calyx:

*Shape.*—Almost cylindrical, widening toward the top.

*Size.*—Medium.

*Shape.*—Medium in breadth and long.

*Aspect.*—Smooth.

*Splitting.*—Sometimes the calyx does split.

Flower stem:
*Length.*—About 65 cm.
*Character.*—Erect and rigid.
*Color.*—145C and 189B.

THE FLOWER

Blooming habit: Recurrent and profuse.
Size of bloom: Medium.
*Diameter.*—About 9 cm. in average with a depth of about 5.5 cm. in average.
Borne: Singly on strong, upright stems.
Shape: When bloom first opens, high centered. When bloom matures, dome-shaped.
Petalage:
*Number of petals.*—About 50 in average.
*Arrangement.*—Imbricated.
*Shape.*—Fan-shaped with apex margin moderately serrated.
*Texture.*—Soft.
*Appearance.*—Satiny.
*Color.*—Outer and Inside Petals: Upper Side: Body — 3D and 4C inconspicuously striated with 50B or 50C and 155D there being about five strias of each color on each petal. Base — Yellowish green. Reverse Side: The same as upper side.
Petaloids: Rarely present.
*Size.*—Smaller than petals.
*Color.*—The same as the petals.
Flower stem:
*Length.*—About 65 cm.
*Color.*—145C and 189B.

*Character.*—Upright and of good strength.
Fragrance: Slight.
Persistence: The petals hang on and dry.
Disease resistance: Resistant to *Fusarium oxysporum* as observed in The Alpes Maritimes area of France.
Lasting quality:
*Vase keeping as a cut flower.*—At least 10 days.

REPRODUCTIVE ORGANS

Stamens:
*Number.*—15 in average, arranged around the ovary.
*Anthers.*—Size: Less than 4 mm. Color: Whitish.
*Filaments.*—Color: Whitish.
Pistils:
*Number.*—2 to 4.
*Styles.*—Color: Greenish white.
*Stigmas.*—Color: Yellowish.
Character of ovaries: Ribbed.

This new carnation most resembles the variety "Alice" (unpatented). Compared with "Alice", however, this new variety of carnation has a bigger flower and a longer stem. Also, the new variety is more resistant than "Alice" to *Fusarium oxysporum.*

We claim:

1. A new and distinctive carnation variety, substantially as herein shown and described, characterized by its high productivity of very light yellow flowers of medium size having fan-shaped petals with thin striae of red and white.

* * * * *